US006916465B2

(12) United States Patent
Panzer et al.

(10) Patent No.: US 6,916,465 B2
(45) Date of Patent: Jul. 12, 2005

(54) DEODORIZING PREPARATIONS CONTAINING NANOSACLE CHITOSANS AND/OR CHITOSAN DERIVATIVES

(75) Inventors: Claudia Panzer, Grevenbroich (DE); Rolf Wachter, Duesseldorf (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 285 days.

(21) Appl. No.: 10/239,553

(22) PCT Filed: Mar. 14, 2001

(86) PCT No.: PCT/EP01/02863

§ 371 (c)(1),
(2), (4) Date: Sep. 23, 2002

(87) PCT Pub. No.: WO01/70191

PCT Pub. Date: Sep. 27, 2001

(65) Prior Publication Data

US 2003/0133891 A1 Jul. 17, 2003

(30) Foreign Application Priority Data

Mar. 23, 2000 (DE) .......................................... 100 14 529

(51) Int. Cl.$^7$ ............................ A61K 7/32; A61K 7/035
(52) U.S. Cl. ........................ 424/65; 424/69; 424/400; 424/401
(58) Field of Search ........................... 424/65, 69, 400, 424/401

(56) References Cited

U.S. PATENT DOCUMENTS

| | | | |
|---|---|---|---|
| 4,172,887 A | 10/1979 | Vanlerberghe et al. | |
| 4,765,976 A | 8/1988 | Grollier et al. | |
| 5,194,262 A | 3/1993 | Goldberg et al. | |
| 5,271,934 A | 12/1993 | Goldberg et al. | |
| 5,770,187 A | * | 6/1998 | Hasebe et al. ................. 424/69 |
| 5,962,663 A | 10/1999 | Wachter et al. | |
| 5,968,488 A | 10/1999 | Wachter et al. | |
| 6,045,785 A | 4/2000 | Wachter et al. | |

FOREIGN PATENT DOCUMENTS

| | | |
|---|---|---|
| DE | 1 165 574 | 8/1960 |
| DE | 2024 051 | 12/1971 |
| DE | 37 13 099 | 10/1987 |
| DE | 44 42 987 | 6/1996 |
| DE | 195 37 001 | 3/1997 |
| DE | 195 40 296 | 4/1997 |
| DE | 196 04 180 | 8/1997 |
| DE | 197 56 377 | 6/1999 |
| DE | 199 62 860 | 6/2001 |
| EP | 0 803 513 | 3/1995 |
| FR | 2 252 840 | 11/1974 |
| FR | 2 701 266 | 8/1994 |
| JP | 10 140418 | 5/1980 |
| JP | 06 3290808 | 11/1988 |
| JP | 07 304643 | 11/1995 |
| WO | WO 98/17241 | 4/1998 |
| WO | WO 00/47177 | 8/2000 |
| WO | WO 01/32751 | 5/2001 |

OTHER PUBLICATIONS

F. Zulli et al. "Preparation and properties of small nanoparticles for skin and hair care" SOFW–Journal, 123 (1997), No. 13, pp. 880,883–885.

Mehnert et al. "Solid Lipid Nanoparticles, A Novel Carrier for Cosmetics and Pharmaceuticals" Pharm. Ind. 59, Nr. 6 (1997), pp. 511–514.

Sannan, et al., "Studies on Chitin, 2*", pp. 3589–3600, Makromol. Chem., vol. 177, (1976).

S. Chilar et al. Micronization of Organic Solids By Rapid Expansion Of Supercritical Solutions, Proceedings World Congress on Particle Technology 3, Brighton, 1998.

J. Falbe, "Surfactants in Consumer Products",pp. 54–125, Springer Verlag, Berlin, 1987.

J. Falbe et al., "Katalysatoren, Tenside und Mineraloladditive (Catalysts, Surfactants and Mineral Oil Additives)", pp. 123–217, Thieme Verlag,Stuttgart,1987.

R. Lochhead et al. "Encyclopedia of Polymers and Thickeners for Cosmetics," Cosmetics & Toiltries, vol. 108, May 1993, pp. 95–135.

Charles Todd et al. "Volatile silicone fluids for cosmetic formulations" Cosmetics and Toiletries vol. 91 Jan. 1976 pp. 29–32.

"Kosmetische Farbemittel" der Farbstoffkommission der Deutschen Forschungsgemeinschaft, Verlag,Chemmie, Weinheim, 1984 pp. 81–106.

* cited by examiner

Primary Examiner—Shelley A. Dodson
(74) Attorney, Agent, or Firm—Daniel S. Ortiz

(57) ABSTRACT

A deodorizing composition containing an ingredient selected from the group consisting of a nanoscale chitosan having a particle diameter of from about 1 to 300 nm, a nanoscale chitosan derivative having a particle diameter of from about 1 to 300 nm, and mixtures thereof.

20 Claims, No Drawings

DEODORIZING PREPARATIONS CONTAINING NANOSACLE CHITOSANS AND/OR CHITOSAN DERIVATIVES

This application is a 371 of PCT/EP01/02863 filed Mar. 14, 2001.

BACKGROUND OF THE INVENTION

This invention relates generally to cosmetic preparations and more particularly to the use of nanoscale chitosans and/or chitosan derivatives in deodorizing preparations.

In the field of personal care, deodorants are used to eliminate unpleasant body odors. Typical examples of such substances are aluminium compounds, such as aluminium sulfate or aluminium chlorohydrate, zinc salts and citric acid compounds. Since the problem of odor inhibition has by no means been completely solved, there is still a need for new preparations which contain dermatologically compatible deodorants with a long-lasting effect.

It is known from DE 19540296C2 that chitosans inhibit the activity of esterase-producing bacteria and that a synergistic deodorizing effect is obtained together with esterase inhibitors and aluminium chlorohydrates. The chitosans have a bacteriostatic effect, i.e. the population of the particular germs is controlled but not killed off in order not to impair the biological equilibrium of the skin flora. The effect of the chitosans or chitosan derivatives and its duration are always associated with the rate at which the compounds are incorporated and absorbed. So far as the compounds hitherto available are concerned, there is considerable potential for improvement in this regard.

The general use of water-soluble chitosan salts in deodorants and antibacterial cosmetics is claimed in Japanese patent application JP 63290808. However, there is a need to further improve the antibacterial activity of chitosans by special formulations.

"Nanonized material" in the context of the present invention is understood to mean spherical aggregates with a diameter of about 1 to about 500 nm which contain at least one solid or liquid core surrounded by at least one continuous membrane. Their use in cosmetics was described in 1997 by Zülli, F. and Suter, F. (Preparation and Properties of Small Nanoparticles for Skin and Hair Care, Seifen-Öle-Fette-Wachse 123 (1997), No. 13, p. 880, 883–885) and by Mehnert, W. et al. (Solid Lipid Nanoparticles, A Novel Carrier for Cosmetics and Pharmaceuticals, Pharm. Ind. 59 (1997), pp. 511–514). The core and membrane may consist of one and the same material or even of different materials.

The processing of auxiliaries and active substances in selected formulations can be simplified by using them in the form of nanoparticles. This applies above all where there is incompatibility with other auxiliaries. In addition, the release and absorption of substances can be controlled through the particle or capsule size, by the use of various auxiliaries or various physicochemical properties.

U.S. Pat. Nos. 5,194,262 and 5,271,934 describe microcapsules containing antiperspirants. These microcapsules acquire bioadhesive properties through constituents of the membrane or even additional coatings and thus contribute to a long-lasting effect.

Accordingly, the problem addressed by the invention was to improve the distribution and uptake of chitosans or chitosan derivatives and at the same time to obtain a long-lasting deodorizing effect. In addition, the biopolymers would lend themselves to simple incorporation in the formulation and their compatibility with anionic auxiliaries would be improved. The final formulation would be distinguished by a pleasant skin feel, high dermatological compatibility and high stability.

DESCRIPTION OF THE INVENTION

The present invention relates to deodorizing preparations which contain nanoscale chitosans and/or chitosan derivatives with a particle diameter in the range from 10 to 300 nm.

It has surprisingly been found that the use of nanoscale chitosan leads to a long-lasting deodorizing effect, that the absorption of chitosans or chitosan derivatives by the Stratum corneum of the skin can be increased and that, in addition, the production of the preparations and their compatibility with anionic surfactants are considerably facilitated by the use of the nanoscale chitosans. The formulations produced have a pleasant feeling on the skin and show high stability. The moisturizing effect of "nanochitosans" counteracts possible drying out of the skin, particularly in the case of alcohol-containing aerosol formulations.

Chitosans and Chitosan Derivatives

Chitosans are biopolymers which belong to the group of hydrocolloids. Chemically, they are partly deacetylated chitins varying in molecular weight which contain the idealized monomer unit:

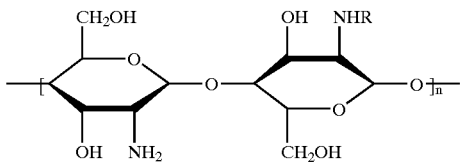

Chitosans are produced from chitin, preferably from the shell remains of crustaceans which are available in large quantities as inexpensive raw materials. Normally, the chitin is first deproteinized by addition of bases, demineralized by addition of mineral acids and, finally, deacetylated by addition of strong bases in a process described for the first time by Hackmann et al., the molecular weights being spread over a broad range. Corresponding processes are known, for example, from Makromol. Chem. 177, 3589 (1976) or French patent application FR 2701266 A1. Preferred types are those described in German patent applications DE 4442987 A1 and DE 19537001 A1 (Henkel) which have an average molecular weight of 800,000 to 1,200,000 dalton, a Brookfield viscosity (1% by weight in glycolic acid) below 5,000 mPas, a degree of deacetylation of 80 to 88% and an ash content of less than 0.3% by weight. Besides chitosans as typical cationic biopolymers, anionically, nonionically or cationically derivatized chitosans, for example the carboxylation, succinylation, alkoxylation or quaternization products described, for example, in German patent DE 3713099 C2 (L"Oreal) and in German patent application DE 19604180 A1 (Henkel), may also be used.

Production of Nanoparticles

One process for the production of nanoparticles by rapid expansion of supercritical solutions (RESS process) is known from the article by S. Chihiar, M. Türk and K. Schaber in Proceedings World Congress on Particle Technology 3, Brighton, 1998. A preferred embodiment of the invention is characterized by the use of nanoscale chitosans and/or chitosan derivatives obtained by (a) dissolving the starting materials in a suitable solvent under supercritical or near-critical conditions, (b) expanding the fluid mixture through a nozzle into a vacuum, a gas or a liquid and (c) simultaneously evaporating the solvent.

To prevent the nanoparticles from agglomerating, it is advisable to dissolve the starting materials in the presence of suitable protective colloids or emulsifiers and/or to expand the critical solutions into aqueous and/or alcoholic solutions of the protective colloids or emulsifiers or into cosmetic oils which may in turn contain redissolved emulsifiers and/or protective colloids. Suitable protective colloids are, for example, gelatine, casein, gum arabic, lysalbinic acid, starch and polymers, such as polyvinyl alcohols, polyvinyl pyrrolidones, polyalkylene glycols and polyacrylates. Accordingly, the nanoscale chitosans and/or chitosan derivatives preferably used are those which are surrounded by a protective colloid and/or an emulsifier. The protective colloids or emulsifiers are normally used in quantities of 0.1 to 20% by weight and preferably in quantities of 5 to 15% by weight, based on the chitosans and/or chitosan derivatives.

Another suitable process for the production of nanoscale particles is the evaporation technique. Here, the chitosans are dissolved in a suitable dilute organic acid or mineral acid, for example glycolic acid, lactic acid or hydrochloric acid at pH values of 1 to 5. The resulting solution is introduced into a nonsolvent for the chitosans (for example alkanes, vegetable oils, cosmetic oils, ethers, esters, ketones, acetals and the like) which may contain a surface-active compound. As a result of the mixing of the two systems, the nanoparticles are precipitated, the aqueous phase preferably evaporating. W/o or o/w microemulsions may be used instead of the aqueous solutions and mixed with the nonsolvent. The emulsifiers and protective colloids mentioned at the beginning may be used as the surface-active compounds. Another method for the production of nanoparticles is the so-called GAS process (gas anti-solvent recrystallization). This process uses a highly compressed gas or supercritical fluid (for example carbon dioxide) as nonsolvent for the crystallization of dissolved substances. The compressed gas phase is introduced into the primary solution of the starting materials and absorbed therein so that there is an increase in the liquid volume and a reduction in solubility and fine particles are precipitated. The PCA process (precipitation with a compressed fluid anti-solvent) is equally suitable. In this process, the primary solution of the starting materials is introduced into a supercritical fluid which results in the formation of very fine droplets in which diffusion processes take place so that very fine particles are precipitated. In the PGSS process (particles from gas saturated solutions), the starting materials are melted by the introduction of gas under pressure (for example carbon dioxide or propane). Temperature and pressure reach near- or super-critical conditions. The gas phase dissolves in the solid and lowers the melting temperature, the viscosity and the surface tension. On expansion through a nozzle, very fine particles are formed as a result of cooling effects.

Commercial Applications

Compared with conventional chitosans and/or chitosan derivatives, the particular fineness of the particles provides for their more rapid penetration into the stratum corneum after topical application. On the other hand, a long-lasting deodorizing effect is also obtained through the slow dissolution of the particles at the point of action. The nanoscale compounds are normally used in a quantity of 0.01 to 5% by weight, preferably in a quantity of 0.1 to 1% by weight and more particularly in a quantity of 0.2 to 0.6% by weight, based on the preparations.

The mean particle sizes (volume distribution) of the nanoparticle used are in the range from 1 to 300 nm, preferably in the range from 10 to 200 nm and more particularly in the range from 50 to 150 nm. The deodorant preparations, such as creams, gels, roll-on, sticks and sprays, obtainable using the nanoscale chitosans and chitosan derivatives in accordance with the invention may additionally contain mild surfactants, oil components, emulsifiers, superfatting agents, stabilizers, consistency factors, thickeners, polymers, silicone compounds, biogenic agents, preservatives, hydrotropes, solubilizers, antioxidants, propellent gases, perfume oils, dyes and the like as further auxiliaries and additives.

Antiperspirants

The antiperspirants of component (b1) are salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxy-allantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Aluminium chlorohydrate, aluminium zirconium tetrachlorohydrate, aluminium zirconium pentachlorohydrate and complex compounds thereof are preferably used. In addition, antiperspirants may contain typical oil-soluble and water-soluble auxiliaries in relatively small amounts. Oil-soluble auxiliaries such as these include, for example, inflammation-inhibiting, skin-protecting or pleasant-smelling essential oils, synthetic skin-protecting agents and/or oil-soluble perfume oils.

The preparations according to the invention may contain the antiperspirants in quantities of 1 to 50, preferably 5 to 30 and more particularly 10 to 25% by weight, based on the solids content.

Esterase Inhibitors

Where perspiration is present in the underarm region, extracellular enzymes—esterases, mainly proteases and/or lipases—are formed by bacteria and split the esters present in the perspiration, releasing odors in the process. Esterase inhibitors of component . . . are preferably trialkyl citrates, such as trimethyl citrate, tripropyl citrate, triisopropyl citrate, tributyl citrate and, in particular, triethyl citrate (Hydagen® CAT, Cognis GmbH, Düsseldorf, FRG). Esterase inhibitors inhibit enzyme activity and thus reduce odor formation. The free acid is probably released by the cleavage of the citric acid ester and reduces the pH value of the skin to such an extent that the enzymes are inactivated by acylation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

The preparations according to the invention may contain the esterase inhibitors in quantities of 0.01 to 20, preferably 0.1 to 10 and more particularly 0.5 to 5% by weight, based on the solids content.

Bactericidal or bacteriostatic agents

A typical example of an additional suitable bactericidal or bacteriostatic agent is phenoxyethanol. 5-Chloro-2-(2,4-dichlorophenoxy)-phenol which is marketed under the name of Irgasan® by Ciba-Geigy, Basle, Switzerland, has also proved to be particularly effective.

The preparation according to the invention may contain the bactericidal or bacteriostatic agents in quantities of 0.01 to 5 and preferably 0.1 to 2% by weight, based on the solids content.

Perspiration Absorbers

Suitable perspiration absorbers are modified starch such as, for example, Dry Flo Plus (National Starch), silicates, talcum and other substances of similar modification which appear suitable for absorbing perspiration.

The preparations according to the invention may contain the perspiration-absorbing substances in quantities of 0.1 to 30% by weight, preferably 1 to 20% by weight and more particularly 5 to 10% by weight, based on the solids content.

Other Auxiliaries and Additives

In order to be able to apply the active components to the skin in a measurable, economical, convenient and cosmetically attractive manner, they are normally incorporated in formulation bases (for typical ingredients, see below). The most important bases include alcoholic and aqueous/alcoholic solutions, emulsions, gels, oils, wax/fat compounds, stick preparations and powders. Other ingredients are superfatting agents, emulsifiers, antioxidants and perfume oils, essential oils, dyes and—for spray applications—propellant gases, such as propane and/or butane for example. The preparations are preferably marketed as rollers (roll-on emulsions), sticks, creams, deodorant or pump sprays.

These preparations may contain mild surfactants, consistency factors, thickeners, stabilizers, polymers, silicone compounds, fats, waxes, lecithins, phospholipids, biogenic agents, film formers, solubilizers, preservatives, dyes and the like as further auxiliaries and additives.

Surfactants

Suitable surfactants are anionic, nonionic, cationic and/or amphoteric or zwitterionic surfactants which may be present in the preparations in quantities of normally about 1 to 70% by weight, preferably 5 to 50% by weight and more preferably 10 to 30% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineral öladditive (Catalysts, Surfactants and Mineral Oil Additives)", Thieme Verlag, Stuttgart, 1978, pages 123–217. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Oil Components

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkylhydroxycarboxylic acids with linear or branched $C_{6-22}$ fatty alcohols (cf. DE 197 56 377 A1), more especially Dioctyl Malate, dialkyl carbonates including, in particular, dioctyl carbonate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di-and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils (cyclomethicone, silicon methicone types, etc.) and/or aliphatic or naphthenic hydrocarbons, for example squalane, squalene or dialkyl cyclohexanes.

Emulsifiers

Suitable emulsifiers are, for example, nonionic surfactants from at least one of the following groups:

- products of the addition of 2 to 30 moles of ethylene oxide and/or 0 to 5 moles of propylene oxide onto linear $C_{8-22}$ fatty alcohols, $C_{12-22}$ fatty acids and alkyl phenols containing 8 to 15 carbon atoms in the alkyl group and alkylamines containing 8 to 22 carbon atoms in the alkyl group;
- alkyl and/or alkenyl oligoglycosides containing 8 to 22 carbon atoms in the alkyl group and ethoxylated analogs thereof;
- addition products of 1 to 15 moles of ethylene oxide onto castor oil and/or hydrogenated castor oil;
- addition products of 15 to 60 moles of ethylene oxide onto castor oil and/or hydrogenated castor oil;
- partial esters of glycerol and/or sorbitan with unsaturated, linear or saturated, branched fatty acids containing 12 to 22 carbon atoms and/or hydroxycarboxylic acids containing 3 to 18 carbon atoms and adducts thereof with 1 to 30 moles of ethylene oxide;
- partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and adducts thereof with 1 to 30 moles of ethylene oxide;
- mixed esters of pentaerythritol, fatty acids, citric acid and fatty alcohol according to DE 11 65 574 PS and/or mixed esters of fatty acids containing 6 to 22 carbon atoms, methyl glucose and polyols, preferably glycerol or polyglycerol,
- mono-, di- and trialkyl phosphates and mono-, di- and/or tri-PEG-alkyl phosphates and salts thereof,
- wool wax alcohols
- polysiloxane/polyalkyl/polyether copolymers and corresponding derivatives,
- block copolymers, for example Polyethyleneglycol-30 Dipolyhydroxystearate;
- polymer emulsifiers, for example Pemulen types (TR-1, TR-2) of Goodrich;
- polyalkylene glycols and
- glycerol carbonate.

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as refatting agents for cosmetic formulations from DE 20 24 051 PS.

Alkyl and/or alkenyl oligoglycosides, their production and their use are known from the prior art. They are produced in particular by reacting glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 moles of ethylene oxide onto the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 moles of ethylene oxide with the sorbitan esters mentioned are also suitable.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Poly-glyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylolpropane or pentaerythritol with lauric acid, cocofatty acid, tallow fatty acid, palmitic acid, stearic acid, oleic acid, behenic acid and the like optionally reacted with 1 to 30 moles of ethylene oxide.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Finally, cationic surfactants are also suitable emulsifiers, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs) and correspond to the following general formula:

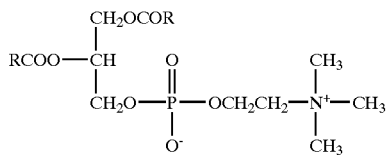

where R typically represents linear aliphatic hydrocarbon radicals containing 15 to 17 carbon atoms and up to 4 cis-double bonds. Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Consistency Factors and Thickeners

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, Amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2 252 840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacryl-amide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. Other suitable polymers and thickeners can be found in Cosmetics & Toiletries, Vol. 108, May 1993, pages 95 et seq.

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Biogenic Agents

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Additional Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers. Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide. The percentage content of the additional germ inhibitors is about 0.1 to 2% by weight, based on the percentage solids content of the preparations.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, limeblossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romilat, irotyl and floramat.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

EXAMPLES

Preparation of the Nanoscale Chitosans and Chitosan Derivatives

In Examples 1 and 2, carbon dioxide was first taken from a reservoir under a constant pressure of 60 bar and was purified in a column with an active carbon and a molecular sieve packing. After liquefaction, the $CO_2$ was compressed to the required supercritical pressure p by a diaphragm pump at a constant delivery rate of 3.5 l/h. The solvent was then brought to the necessary temperature T1 in a preheater and was introduced into an extraction column (steel, 400 ml) charged with the chitosan or chitosan derivative. The resulting supercritical, i.e. fluid, mixture was sprayed through a laser-drawn nozzle (length 830 μm, diameter 45 μm) at a temperature T2 into a Plexiglas expansion chamber containing a 4% by weight aqueous solution of an emulsifier or protective colloid. The fluid medium evaporated, leaving the dispersed nanoparticles encapsulated in the protective colloid behind. The process conditions and the average particle size range (PSR, as determined photometrically by the 3-WEM method) are set out in Table 1 below.

TABLE 1

Production parameters for nanoparticles

| Ex. | Chitosan (derivative) | Solv. | p bar | T1 °C. | T2 °C. | Emulsifier/ Protective Colloid | PSR nm |
|---|---|---|---|---|---|---|---|
| 1 | Chitosan | $CO_2$ | 200 | 85 | 180 | Polyvinyl alcohol | 70–140 |
| 2 | Chitosan Succinate | $CO_2$ | 200 | 85 | 175 | Polyvinyl alcohol | 50–150 |

TABLE 2a

Antiperspirant or deodorant suspension sticks and soft solids - quantities = % by weight

| Composition | 1 | 2 | 3 | 4 | 5 | 6 |
|---|---|---|---|---|---|---|
| Nanochitosan of Example 1 in Table 1 | 0.1 | 0.2 | 0.4 | 0.6 | 0.3 | 0.5 |
| Distearyl ether | — | 15 | — | — | — | — |
| Stearyl alcohol | — | — | 10 | 10 | 14.7 | — |
| Guerbet alcohol C36 | 15 | — | — | — | — | — |
| Tribehenin | — | — | — | — | — | 20 |
| Hyrogenated Castor Oil | — | — | — | — | 3.7 | — |
| Dioctyl carbonate | 20 | 60 | 60 | 60 | 58.7 | 55 |
| Octyl dodecanol | 10 | — | — | — | — | — |
| Dicaprylyl ether | 10 | — | — | — | — | — |
| Hexyl decanol + Hexyldecyl Laurate | 10 | — | — | — | — | — |
| Cyclomethicone | 10 | — | — | — | — | — |
| Dry Flo Plus* | — | — | 5 | — | — | — |
| Silica | — | — | — | 2.5 | — | — |
| Talcum | — | — | — | 2.5 | — | — |
| Aluminium Zirconium Tetrachlorohydrex GLY | — | — | 25 | — | — | — |
| Aluminium Chlorohydrate | 25 | — | — | — | — | — |
| Rub-off color | White | White | White | White | White | White |
| Hardness** | 4.2 | 4.2 | 5.0 | 4.9 | 4.2 | 4.6 |
| Oil secretion | No | No | No | No | No | No |

TABLE 2a-continued

Antiperspirant or deodorant suspension sticks and soft solids - quantities = % by weight

| Composition | 1 | 2 | 3 | 4 | 5 | 6 |
|---|---|---|---|---|---|---|
| Feeling on the skin | Particularly velvety, soft, powdery, dry | Particularly velvety, soft, powdery, dry | Particularly velvety, soft, powdery, particularly dry, not oily at beginning | Particularly velvety, soft, powdery, particularly dry | Particularly velvety, soft, powdery, dry | Soft, creamy, powdery |

*National Starch
**As measured with a Penetrometer PNR 10 Petrotest

TABLE 2b

Antiperspirant or deodorant suspension sticks and soft solids - quantities = % by weight

| Composition | 7 | 8 | 9 | 10 | 11 |
|---|---|---|---|---|---|
| Nanochitosan of Example 2 in Table 1 | 0.4 | 0.3 | 0.5 | 0.2 | 0.2 |
| 12-Hydroxy-stearic acid | 10 | 5 | 8 | — | 10 |
| Dibutyl Lauroyl Glutamide | — | — | 2 | — | — |
| Distearyl ether | — | — | — | — | — |
| Stearyl alcohol | — | — | — | 18 | — |
| Tribehenin | — | — | — | — | — |
| Hydrogenated Castor Oil | — | — | — | 5 | — |
| Dioctyl Carbonate | 65 | 65 | 65 | — | — |
| Octyl dodecanol | — | — | — | 15 | 15 |
| Cyclomethicone | — | — | — | 37 | 50 |
| Dry Flo Plus* | — | 5 | — | — | — |
| Silica | — | — | — | — | — |
| Talcum | — | — | — | — | — |
| Aluminium Zirconium Tetra-chlorohydrex GLY | — | — | — | — | 25 |
| Aluminium Chlorohydrate | — | — | — | 25 | — |
| Rub-off color | Transparent | Transparent | Transparent | Strong white | Transparent |
| Hardness** | 4.0 | 5.0 | 4.0 | 4.1 | 4.0 |
| Oil secretion | No | No | No | No | No |
| Feeling on the skin | Particularly velvety, soft, powdery, dry | Particularly velvety, soft, powdery, particularly dry, not oily at beginning | Particularly velvety, soft, powdery, dry | Wax-like, dry | Soft, slightly powdery |

*National Starch
**As measured with a Penetrometer PNR 10 Petrotest

The emulsification properties and stability of the preparations according to the invention were subjectively evaluated (+=very good, −=satisfactory).

TABLE 3

Deodorant creams - quantities in % by weight

| Composition | 1 | 2 | 3 | 4 |
|---|---|---|---|---|
| Nanochitosan of Example 1 in Table 1 | 0.2 | 0.2 | 0.2 | 0.2 |
| Emulgade SE-PF* | 6.0 | 6.0 | 6.0 | 6.0 |
| Sodium Cetearyl Sulfate | 0.5 | 0.5 | 0.5 | 0.5 |
| Cetearyl alcohol | 1 | 1 | – | – |
| Behenyl alcohol | 3 | 3 | 4 | 4 |
| Dioctyl carbonate | 6.0 | 3 | 9.0 | 9.0 |
| Cyclomethicone | 3.0 | 2 | – | – |
| Octyl dodecanol | – | 1 | – | – |
| Dicaprylyl ether | – | 2 | – | – |
| Hexyldecanol + Hexyldecyl Laurate | – | 1 | – | – |
| Farnesol | – | – | – | 0.2 |
| Triethyl citrate | – | – | – | 1.5 |
| Talcum | – | 10.0 | 10.0 | – |
| Water, demin. | to | to | to | to |
| Emulsification properties | + | + | + | + |
| Homogeneous distribution | + | + | + | + |

TABLE 3-continued

Deodorant creams - quantities in % by weight

| Composition | 1 | 2 | 3 | 4 |
|---|---|---|---|---|
| of active principle | | | | |
| Stability | + | + | + | + |
| Feeling on the skin | Very velvety, soft | Very velvety, soft | Particularly velvety, soft, powdery and caring | Very velvety, soft |

*COGNIS

The emulsification properties and stability of the preparations according to the invention were subjectively evaluated (+=very good, −=satisfactory).

TABLE 3

Oil-in-water emulsions for roll-on and sprayable antiperspirant/deodorant applications - quantities in % by weight

| Composition | 1 | 2 | 3 | 4 |
|---|---|---|---|---|
| Nanochitosan of Example 2 in Table 1 | 0.1 | 0.1 | 0.3 | 0.1 |
| Emulgade SE-PF* | 4.1 | 4.1 | – | – |
| Ceteareth-20 | 0.9 | 0.9 | 1.5 | 1.5 |
| Ceteareth-10 | – | – | 1.5 | 1.5 |
| Glyceryl Stearate | – | – | 5.0 | 5.0 |
| Cetyl Alcohol | – | – | 3.0 | 3.0 |
| Dioctyl carbonate | 10.0 | 3 | 3.0 | 3.0 |
| Cyclomethicone | – | 2 | – | – |
| Octyl dodecanol | – | 2 | – | – |
| Dicaprylyl ether | – | 2 | – | – |
| Hexyl decanol + Hexyldecyl Laurate | – | 1 | – | – |
| Triethyl citrate | – | – | – | 0.5 |
| Water, demin. | to 100 | to 100 | to 100 | to 100 |
| Emulsification properties | + | + | + | + |
| Stability | + | + | + | + |
| Feeling on the skin | Quickly absorbed, fairly dry caring skin feel | Quickly absorbed, fairly dry caring skin feel | Less caring, less dry skin feel | Quickly absorbed, fairly dry caring skin feel |

*Cognis

TABLE 5

Deodorant aerosol applications - quantities in % by weight

| Composition | 1 | 2 | 3 | 4 | 5 | 6 |
|---|---|---|---|---|---|---|
| Nanochitosan of Example 2 in Table 1 | 0.2 | 0.4 | 0.1 | 0.1 | 0.1 | 0.1 |
| LPG 2,7 | | 45 | 50 | | 48 | 50 |
| Drivosol 3,5 | 40 | | | 45 | | |
| Isopentane | 20 | 20 | | 10 | 20 | 25 |
| Diethyl ether | | | 5 | 5 | 5 | |
| Isopropyl palmitate | 15 | — | — | — | 10 | 12 |
| Dicapryl ether | — | 18 | — | — | — | 7.9 |
| Hexyl decanol + hexyl decyl laurate | — | — | 15 | — | — | — |
| Squalane | — | — | — | 10 | — | — |
| Ethanol | 20 | 15 | — | — | — | — |
| Isopropanol | — | — | 20 | 15 | — | — |
| Cyclomethicone | 4.8 | 1.6 | 4.9 | 9.9 | 4.9 | — |
| Aluminium Zirconium Tetrachlorohydrex GLY | — | — | 5 | — | — | — |
| Aluminium Chlorohydrate | — | — | — | 5 | — | — |
| Triethyl Citrate | — | — | — | — | 2 | — |
| Talcum | — | — | — | — | 10 | 5 |
| Emulsification properties | + | + | + | + | + | + |
| Stability | + | + | + | + | + | + |
| Skin feel | + | + | + | + | + | + |

What is claimed is:

1. A deodorizing composition comprising a particulate ingredient selected from the group consisting of nanoscale chitosan having an average particle size range of from about 1 to 300 nm, nanoscale chitosan derivatives having an average particle size range of from about 1 to 300 nm, and mixtures thereof, wherein the particulate ingredient is prepared by a process which comprises:
   (a) dissolving the chitosan or chitosan derivative starting material in a solvent for the material to form a fluid mixture at supercritical or near supercritical conditions;
   (b) expanding the fluid mixture into a vacuum, a gas or a liquid while simultaneously evaporating the solvent to form the particles.

2. The composition of claim 1 wherein the particulate has an average particle size range of from about 10 to 200 nm.

3. The composition of claim 1 wherein the particulate ingredient has an average particle size range of from about 50 to 150 nm.

4. The composition of claim 1 wherein the particulate ingredient has a molecular weight of from about 50,000 to 2,000,000.

5. The composition of claim 1 wherein the nanoscale chitosan derivative comprises a member selected from the group consisting of anionically derivatized chitosan, non-ionically derivatized chitosan, cationically derivatized chitosan, and mixtures thereof.

6. The composition of claim 1 wherein the particulate ingredient is present in the composition in an amount of from about 0.01 to 5% by weight, based on the weight of the composition.

7. The composition of claim 1 wherein the particulate ingredient is present in the composition in an amount of from about 0.1 to 1% by weight, based on the weight of the composition.

8. The composition of claim 1 wherein the particulate ingredient is present in the composition in an amount of from about 0.2 to 0.6% by weight, based on the weight of the composition.

9. The composition of claim 1 further comprising an auxiliary ingredient selected from the group consisting of an esterase inhibitor, a bactericidal agent, a bacteriostatic agent, an oil component, an antiperspirant, a perspiration absorber, and mixtures thereof.

10. A process for inhibiting body odor formation comprising contacting human skin with a deodorizing composition containing a particulate ingredient selected from the group consisting of a nanoscale chitosan having an average particle size range of from about 1 to 300 nm, nanoscale chitosan derivatives having an average particle size range of from about 1 to 300 nm, and mixtures thereof, wherein the particulate ingredient is prepared by a process which comprises:
   (a) dissolving the chitosan or chitosan derivative starting material in a solvent for the material to form a fluid mixture at supercritical or near supercritical conditions;
   (b) expanding the fluid mixture into a vacuum, a gas or a liquid while simultaneously evaporating the solvent to form the particles.

11. The process of claim 10 wherein the particulate ingredient has an average particle size range of from about 10 to 200 nm.

12. The process of claim 10 wherein the particulate ingredient has an average particle size range of from about 50 to 150 nm.

13. The process of claim 10 wherein the particulate ingredient has a molecular weight of from about 50,000 to 2,000,000.

14. The process of claim 10 wherein the nanoscale chitosan derivative comprises a member selected from the group consisting of anionically derivatized chitosan, nonionically derivatized chitosan, cationically derivatized chitosan, and mixtures thereof.

15. The process of claim 10 where the particulate ingredient is present in the composition in an amount of from about 0.1 to 5% by weight, based on the weight of the composition.

16. The process of claim 10 wherein the particulate ingredient is present in the composition in an amount of from about 0.1 to 1% by weight, based on the weight of the composition.

17. The process of claim 10 wherein the particulate ingredient is present in the composition in an amount of from about 0.2 to 0.6% by weight, based on the weight of the composition.

18. The process of claim 10 further comprising an auxiliary ingredient selected from the group consisting of esterase inhibitors, bactericidal agents, bacteriostatic agents, oil components, antiperspirants, perspiration absorbers, and mixtures thereof.

19. The composition of claim 1 wherein the fluid mixture is expanded into a liquid containing a protecting colloid.

20. The composition of claim 1 wherein the liquid comprises water.

* * * * *